US008470885B2

(12) United States Patent
Szewczyk

(10) Patent No.: US 8,470,885 B2
(45) Date of Patent: Jun. 25, 2013

(54) COMPOSITION AND METHOD FOR TREATMENT OF DIABETES

(75) Inventor: Jerzy Ryszard Szewczyk, Chapel Hill, NC (US)

(73) Assignee: Biokier, Inc., Chapel Hill, NC (US)

( * ) Notice: Subject to any disclaimer, the term of this patent is extended or adjusted under 35 U.S.C. 154(b) by 132 days.

(21) Appl. No.: 13/143,766

(22) PCT Filed: Jan. 11, 2010

(86) PCT No.: PCT/US2010/020629
§ 371 (c)(1),
(2), (4) Date: Jul. 8, 2011

(87) PCT Pub. No.: WO2010/081079
PCT Pub. Date: Jul. 15, 2010

(65) Prior Publication Data
US 2011/0275716 A1    Nov. 10, 2011

Related U.S. Application Data

(60) Provisional application No. 61/143,951, filed on Jan. 12, 2009, provisional application No. 61/293,773, filed on Jan. 11, 2010.

(51) Int. Cl.
*A61K 31/195* (2006.01)
(52) U.S. Cl.
USPC .......................................... 514/563; 514/557
(58) Field of Classification Search
USPC .................................. 514/563, 557
See application file for complete search history.

(56) References Cited

U.S. PATENT DOCUMENTS

| 6,548,083 | B1 | 4/2003 | Wong et al. |
| 6,652,882 | B1 | 11/2003 | Odidi et al. |
| 7,431,943 | B1 | 10/2008 | Villa et al. |
| 7,799,782 | B2 * | 9/2010 | Munson et al. ............ 514/234.5 |
| 2003/0203004 | A1 | 10/2003 | Kelm et al. |
| 2004/0132669 | A1 | 7/2004 | Nishimura et al. |
| 2006/0134208 | A1 | 6/2006 | Villa et al. |
| 2006/0159749 | A1 | 7/2006 | Villa et al. |
| 2007/0032529 | A1 | 2/2007 | Takagi et al. |
| 2007/0060759 | A1 | 3/2007 | Cotticelli et al. |
| 2010/0130426 | A1 | 5/2010 | Young et al. |
| 2010/0130472 | A1 | 5/2010 | Young et al. |
| 2010/0311834 | A1 | 12/2010 | Manku et al. |
| 2011/0034555 | A1 | 2/2011 | Osterloh et al. |
| 2011/0071176 | A1 | 3/2011 | Rowe |

FOREIGN PATENT DOCUMENTS

| EP | 1790333 A1 | 5/2007 |
| WO | 9921536 | 5/1999 |
| WO | 0076478 | 12/2000 |
| WO | 2005/074718 A1 | 8/2005 |
| WO | 2005074718 A1 | 8/2005 |
| WO | 2006/003043 A1 | 1/2006 |
| WO | 2006003043 A1 | 1/2006 |
| WO | 2007036363 A2 | 4/2007 |
| WO | 2007127505 A2 | 11/2007 |
| WO | 2008067219 A2 | 6/2008 |
| WO | WO2008/071790 | * 6/2008 |
| WO | 2010/062861 A2 | 6/2010 |
| WO | 2010/062863 A1 | 6/2010 |
| WO | 2010062861 A2 | 6/2010 |
| WO | 2010062863 A2 | 6/2010 |

OTHER PUBLICATIONS

Wendling A, Wudyka A. "Narcotic addiction following gastric bypass surgery—a case study." Obes Surg. May 2011;21 (5):680-3. PMID: 20473721 [PubMed—indexed for MEDLINE].
Gwen Tolhurst, Frank Reimann and Fiona M. Gribble. "Nutritional regulation of glucagon-like peptide-1 secretion." DOI: 10.1113/jphysiol.2008.164012. J Physiol 587.1 (2009) pp. 27-32.
Spencer, Alcohol addiction risk after bariatric surgery?, The Wall Street Journal, Jul. 18, 2006.
Saules et al., Bariatric surgery history among substance abuse treatment patients: prevalence and associated features, Elsevier, Oct. 19, 2009.
Greenberg et al., Behavioral and Psychological care in Weight Loss Surgery: Best Practice Update, Intervention and Prevention, The Lehman Series, vol. 17, No. 5, May 2009.
Odom et al., Behavioral Predictors of Weight Regain after Bariatric Surgery, Feb. 28, 2009.
Bupropion, Wikipedia, http://en.wikipedia.org/wiki/Bupropion, May 30, 2009.
Gadde et al., Bupropion for Weight Loss: An Investigation of Efficacy and Tolerability in Overweight and Obese Women, Obesity Research, vol. 9, No. 9, Sep. 2001.
Wischmeyer et al., Chronic Pouchitis After Ileal Pouch-Anal Anastomosis: Responses to Butyrate and Glutamine Suppositories in a Pilot Study, Mayo Foundation for Medical Education and Research, pp. 978-981, 1993.
Lili et al., Combination of GLP-1 and sodium butyrate promote differentiation of pancreatic progenitor cells into insulin-producing cells, Tissue and Cell, Elsevier, 2008.
Toft-Nielsen et al., Determinants of the Impaired Secretion of Glucagon-Like Peptide-1 in Type 2 Diabetic Patients, The Journal of Clinical Endocrinology & Metabolism, The Endocrine Society, 2001.
Category: Dopamine reuptake inhibitors, Wikipedia, http://en.wikipedia.org/wiki/Category: Dopamine_reuptake_inhibitors, May 30, 2009.
Leahey et al., Effects of bariatric surgery on food cravings: do food cravings and the consumption of craved foods "normalize" after surgery?, Elsevier, 2012.
glucagon.com, http://www.glucagon.com/index.html, Jun. 25, 2009.
Reimann et al., Glutamine potently stimulates glucagon-like peptide-1 secretion from GLUTag cells, Diabetologia, 2004.
Thaler et al., Hormonal and Metabolic Mechanisms of Diabetes Remission After Gastrointestinal Surgery, Endocrinology, Apr. 16, 2009.
Rask et al., Impaired Incretin Response After a Mixed Meal Is Associated With Insulin Resistance in Nondiabetic Men, Diabetes Care, vol. 24, No. 9, Sep. 2001.

(Continued)

*Primary Examiner* — Rei-tsang Shiao
(74) *Attorney, Agent, or Firm* — James G. Passé; Passé Intellectual Property, LLC

(57) ABSTRACT

The present invention relates to a method of treating an incretin related disease such as diabetes, obesity and the like by delivery of butyric acid, bile acid, long chain fatty acid, or glutamine to the colon by bypassing the upper digestive tract.

12 Claims, No Drawings

OTHER PUBLICATIONS

Deacon, Incretin-based treatment of type 2 diabetes: glucagon-like peptide-1 receptor agonists and dipeptidyl peptidase-4 inhibitors, Department of Biomedical Sciences, Panum Institute, University of Copenhagen, Denmark, pp. 23-31, 2007.

Wendling et al., Narcotic Addiction Following Gastric Bypass Surgery—A Case Study, May 16, 2010.

Higa et al., Narcotic Withdrawal Syndrome Following Gastric Bypass—A Difficult Diagnosis, Obesity Surgery, pp. 631-634, 2011.

Appelhans, Neurobehavioral Inhibition of Reward-driven Feeding: Implications for Dieting and Obesity, Behavior and Psychology, vol. 17, No. 4, Apr. 2009, www.obesityjournal.org.

Category: Norepinephrime reuptake inhibitors, Wikipedia, http://en.wikipedia.org/wiki/Category:Norepinephrine_reuptake_inhibitors, May 30, 2009.

Song et al., Nutritional and Psychological Considerations After Bariatric Surgery, Aesthetic Surgery Journal, vol. 28, No. 2, Mar./Apr. 2008, pp. 195-199.

Tolhurst et al., Nutritional regulation of glucagon-like peptide-1 secretion, Symposium Report, pp. 27-32, 2009.

Greenfield et al., Oral glutamine increases circulating glucagon-like peptide 1, glucagon, and insulin concentrations in lean, obese, and type 2 diabetic subjects, AJCN, Dec. 3, 2008.

Biokier Inc., Search Report and Written Opinion to Corresponding PCT Application No. 2010/020629.

Sarwer et al., Psychosocial and Behavioral Aspects of Bariatric Surgery, Obesity Research, vol. 13, No. 4, Apr. 2005, pp. 639-648.

Kalarchian et al., Psychiatric Disorders Among Bariatric Surgery Canidates: Relationship to Obesity and Functional Health Status, Feb. 2007.

Marcus et al., Psychiatric Evaluation and Follow-Up of Bariatric Surgery Patients, Treatment in Psychiatry, Mar. 2009.

Sawyer et al., Psychological Issues Following Bariatric Surgery, Primary Psychiatry, Aug. 2008, pp. 50-55.

Substance Abuse, Obesity (2009) 17, 880-884.

Wellbutrin, Drugs.com, http://www.drugs.com/wellbutrin.html, May 28, 2009.

Wischmeyer et al. "Chronic Pouchitis After Ileal Pouch-Anal Anastomosis: Responses to Butyrate and Glutamine Suppositories in a Pilot Study." Mayo Clin. Proc. 1993, vol. 68, 978.

Carolyn F. Deacon "Incretin-based treatment of type 2 diabetes: glucagon-like peptide-1 receptor agonists and dipeptidyl peptidase-4 inhibitors." Diabetes, Obesity and Metabolism, 9 (Suppl. 1), 2007, 23-31.

Toft-Nielsen MB, Damholt MB, Madsbad S et al. "Determinants of the impaired secretion of glucagon-like peptide-1 in type 2 diabetic patients." J Clin Endocrinol Metab 2001;86:3717-3723.

Rask E, Olsson T, Soderberg S et al. "Impaired incretin response after a mixed meal is associated with insulin resistance in nondiabetic men." Diabetes Care 2001;24:1640-1645.

Jerry R. Greenfield, et al. "Oral glutamine increases circulating glucagon-like peptide 1, glucagon, and insulin concentrations in lean, obese, and type 2 diabetic subjects." American Journal of Clinical Nutrition, Epub Dec. 3, 2008, vol. 89, No. 1, pp. 106-113, ISSN 1938-3297 (electronic).

F. Reimann, et al. "Glutamine potently stimulates glucagon-like peptide-1 secretion from GLUTag cells." Diabetologia, 2004 vol. 47, pp. 1592-1601, ISSN 0012-186X.

Li Li et al, Combination of GLP-1 and sodium butyrate promote differentiation of pancreatic progenitor cells into insulin-producing cells. Tissue and Cell, 2008, vol. 40, pp. 437-445, ISSN 0040-8166.

Samocha-Bonet et al, Glutamine Reduces Postprandial Glycemia and Augments the Glucagon-Like Peptide-1 Response in Type 2 Diabetes Patients, The Journal of Nutrition, Jul. 2011, p. 1233-8; vol. 141 (7), US.

* cited by examiner

COMPOSITION AND METHOD FOR TREATMENT OF DIABETES

This application claims priority of U.S. provisional application 61/143,951 filed on Jan. 12, 2009 and U.S. provisional application 61/293,773 filed on Jan. 11, 2010 and are included herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a novel method and composition for treating diabetes, metabolic syndrome, hypertriglyceridemia, and obesity. In particular, the present invention relates to the treatment of diabetes, metabolic syndrome, hypertriglyceridemia and obesity by delivering specific naturally occurring compounds to the lower gut or rectally.

2. Description of Related Art

Diabetes mellitus is a worldwide health threat of increasing magnitude, and is considered a major health risk both in developed and in developing countries. Type II diabetes accounts for the vast majority of the cases involving diabetes and accounts suggest it is the seventh leading cause of death in the United States. It appears that the major contributing factor to the incidence of Type II diabetes is being overweight. In the United States alone, it is estimated that over 17.6 million individuals suffer from diabetes, and it is estimated that an additional 5.7 million individuals are unaware they have diabetes. In addition, there are about 57 million Americans who are considered pre-diabetic.

Type II diabetes is also known as non-insulin dependent diabetes. It generally manifests itself as an inability to adequately regulate blood-glucose levels. This is as opposed to Type I diabetes which is characterized by defects in pancreatic production of insulin. In other words, it appears that Type II sufferers suffer from too little insulin or insulin resistance. The factors that have been identified in contributing to these Type II factors include one or more of obesity, genetic background, age, diet, and blood chemistry. Type II is frequently called adult onset but because diet is a factor, it can arise at virtually any age.

The results of diabetes Type II cause glucose levels to rise in the blood and urine which in turn can cause hunger, urination, thirst and metabolism related issues. If the condition is not treated, the most common serious results include heart, disease, kidney disease, and blindness. Several treatments are currently being used. Because obesity is frequently a causal agent in diabetes, diet and exercise are usually a front line defense. Therapeutic agents are also used as a second line of defense, including use of insulin or pharmaceuticals that reduce blood and urine levels of glucose.

Several drugs are in current use for diabetes Type II, including insulin secretagogues, glucose lowering effectors, GLP-1 analogs, DPPIV, activators of the peroxisome proliferator activated receptor-gamma and alpha-glucosidase inhibitors. Because these current treatments have several problems associated with them, there is still a need for alternative therapies to treat type II diabetes.

Gut hormones are a type of gastrointestinal hormone that, among others, cause an increase in the amount of insulin released from the beta cells of the islets of Langerhans after eating, even before blood glucose levels become elevated. They are secreted in their highest level from L-cells in the colon. They also slow the rate of absorption of nutrients into the blood stream by reducing gastric emptying and may directly reduce food intake. They also inhibit glucagon release from the alpha cells of the Islets of Langerhans. Glucagon like peptide-1 (GLP-1), which is frequently called an incretin, is a gut hormone secreted by L cells. Glucagon like peptide-1 (GLP-1) (an incretin) has been identified as one composition that if its secretion is stimulated can possibly be used to treat diabetes.

GLP-1 is a peptide secreted from enteroendocine L cells, and has a wide variety of physiological effects that have been described in numerous publications over the past two decades. More recently, much research has been focused on the use of GLP-1 in the treatment of conditions and disorders, such as diabetes mellitus, stress, obesity, appetite control and satiety, Alzheimer's, inflammation, and diseases of the central nervous system. However, the use of a peptide in clinical treatment is severely limited due to difficult administration, and in vivo stability. Therefore, a small molecule that either mimicked the effects of GLP-1 directly, or increased GLP-1 secretion, has been thought to be the treatment of choice in increasing incretin production in treatment of the variety of conditions or disorders described above, namely diabetes mellitus and obesity.

PYY is a gut hormone (Peptide YY) which is a short (36 amino acid) protein released by cells in the ileum and colon in response to feeding. In humans, it appears to reduce appetite. PYY is found in L-cells in the mucosa of the gastrointestinal trace especially in the ileum and colon. There is also a small amount of PYY about 1-10 percent in the esophagus, the stomach, the duodenum, and jejunum. PYY concentration in the circulation increases postprandially (after food ingestion) and decreases by fasting.

GLP-2 (a gut hormone) is a 33 amino acid peptide, co-secreted along with GLP-1 from intestinal endocrine cells in the small and large intestine. GLP-2, among others, stimulates mucosal growth in the small and large intestine, inhibits gastric emptying, and gastric acid secretion, reduces intestinal permeability, and stimulates intestinal blood flow.

Oxyntomodulin (a gut hormone) is a 37 amino acid peptide co-secreted along with GLP-1 from L-cells that mimics the effects of GLP-1 and GLP-2 on gastric acid secretion and gut motility, suppresses appetite and reduces food intake in normal humans and reduces energy intake by ~17%, in overweight and obese human subjects with no effect on water intake.

Butyric acid is a naturally occurring fatty acid occurring in the form of esters in animal fats and plant oils. For example, the triglyceride of butyric acid makes up 3% to 4% of butter. It is found in rancid foods, such as butter and cheese, and has a very unpleasant smell and taste. It is an important member of the fatty acid sub-group called the short chain fatty acids.

Bile acids (also known as bile salts) are steroid acids found predominantly in the bile of mammals. In humans, taurocholic acid and glycocholic acid (derivatives of cholic acid) represent approximately eighty percent of all bile acids. The two major bile acids are cholic acid and chenodeoxycholic acid. They, their conjugates, and their 7-alpha-dehydroxylated derivatives are all found in human intestinal bile. An increase in bile flow is exhibited with an increased secretion of bile acids. Bile acid's main function is to facilitate the formation of micelles, which promotes dietary fat processing.

Bile salts constitute a large family of molecules, composed of a steroid structure with four rings, a five, or eight carbon side-chain terminating in a carboxylic acid, and the presence and orientation of different numbers of hydroxyl groups. The four rings are labeled from left to right (as commonly drawn) A, B, C, and D, with the D-ring being smaller by one carbon than the other three. The hydroxyl groups have a choice of being in 2 positions, either up (or out) termed beta (often drawn by convention as a solid line), or down, termed alpha (seen as a dashed line in drawings). All bile acids have a hydroxyl group on position 3, which was derived from the parent molecule, cholesterol. In cholesterol, the 4 steroid rings are flat and the position of the 3-hydroxyl is beta.

Long chain fatty acids (LCFA) are fatty acids with aliphatic tails of 16 carbons or more. Fatty acids are aliphatic monocarboxylic acids, derived from, or contained in esterified form in an animal or vegetable fat, oil, or wax. Natural fatty acids commonly have a chain of 4 to 28 carbons (usually unbranched and even numbered), which may be saturated or unsaturated.

Glutamine is an amino acid that is used as a nutritional supplement in the treatment of a variety of diseases, including cancer. Glutamine is the most abundant free amino acid in the human body and, in addition to its role as a component of protein, serves a variety of functions in the body. It is a non-essential amino acid because it is made by body cells. In addition, most dietary protein contains ample amounts of glutamine, and healthy people usually obtain all the additional glutamine that they need in their diet.

A number of new approaches to stimulation of the receptors which appear to stimulate gut hormones, such as the GPR 120, TGR5, GPR 41, and GPR 43 receptors are being tried. In patent applications: WO/2008/067219 published Jun. 5, 2008; US2007/060759 published Nov. 8, 2007; JP2006-630 4A published Mar. 9, 2006; and JP 2006-56881 A published Mar. 2, 2006; there are disclosed several classes of small molecules agonists that have been designed to stimulate the TGR5 receptor, a bile acid G-protein-coupled receptor.

The above naturally occurring products are difficult to administer orally with the colon being the target for pharmacological action, especially because taste of these products is extremely unpalatable, and they are easily degraded in the digestive tract and/or absorbed.

Obesity is a medical condition that is reaching epidemic proportions among humans in a number of countries throughout the world. It is a condition that is also associated with, or induces other diseases or conditions that disrupt life's activities and lifestyles. Obesity is recognized as a serious risk factor for other diseases and conditions, such as diabetes, hypertension, and arteriosclerosis, and can contribute to elevated levels of cholesterol in the blood. It is also recognized that increased body weight due to obesity can place a burden on joints, such as knee joints, causing arthritis, pain, and stiffness. Obesity can contribute to certain skin conditions, such as atopic dermatitis and bed sores. Because overeating and obesity have become such a problem in the general population, many individuals are now interested in losing weight, reducing weight, and/or maintaining a healthy body weight and lifestyle.

Hypertriglyceridemia (hTG) is a common disorder in the United States. The condition is exacerbated by uncontrolled diabetes mellitus, obesity, and sedentary habits, all of which are more prevalent in industrialized societies, particularly the United States, than in developing nations. In both epidemiologic and interventional studies, hypertriglyceridemia is a risk factor for coronary artery disease (CAD). Treatment of hypertriglyceridemia is by restriction of carbohydrates and fats in the diet, as well as with niacin, fibrates and statins (three classes of drugs). Increased fish oil intake may substantially lower an individual's triglycerides.

There are obviously a number of compositions designed to deliver a medicament to the lower gut. One in particular are the three-component matrix structures, such as disclosed in U.S. Pat. No. 7,431,943 to Villa et al. issued Oct. 7, 2008 and incorporated herein in its entirety by reference.

A number of different formulations are available for delivery of desired compositions to the colon including amylose coated tablets, enterically coated chitosan tablets, matrix within matrix or multimatrix systems, or poly-saccharide coated tablets. One example of multimatrix controlled release systems are disclosed in U.S. Pat. No. 7,431,943 issued Oct. 7, 2008 to Villa et al. and incorporated herein by reference. Disclosed is a matrix within matrix design wherein a lipophilic phase and amphiphilic phase are incorporated within the inner matrix and at least a portion of the active ingredient is incorporated into the amphiphilic phase.

BRIEF SUMMARY OF THE INVENTION

The present invention relates to the discovery that certain naturally occurring compositions can be delivered to the colon or rectally bypassing the stomach and upper digestive system and increase the production of certain gut hormones from L cells.

Therefore, in one embodiment, the present invention therefore is a method of treating or preventing a condition or disorder affected by the decrease or lack of release of a gut hormone secreted from L cells by stimulating the production of an L cell secreted gut hormone in the colon of an individual comprising:
  a) selecting an agent causing gut hormone secretion from L-cells from the group comprising butyric acid, a bile acid, a long chain fatty acid and glutamine, the composition formulated to release in a colon targeted delivery system or in a rectal release system; and
  b) administering sufficient stimulating pharmaceutical composition to the individual sufficient to cause a release of gut hormones from the L-cell in the colon of the individual sufficient to achieve the desired result.

DETAILED DESCRIPTION OF THE INVENTION

While this invention is susceptible to embodiment in many different forms, there is shown in the drawings and will herein, be described in detail specific embodiments, with the understanding that the present disclosure of such embodiments is to be considered as an example of the principles and not intended to limit the invention to the specific embodiments shown and described. In the description below, like reference numerals are used to describe the same, similar, or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or", as used herein, is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures, if any are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein, the term "treating" refers to alleviating the specified condition, eliminating or reducing the symptoms of the condition, slowing or eliminating the progression of the condition and preventing or delaying the initial occurrence of the condition in a subject, or reoccurrence of the condition in a previously afflicted subject.

As used herein, a "condition or disorder" refers to any disease state, a particular state of a mammal or the like to which an increase in the production of a gut hormone from L cells would affect in a positive or negative way. Included are the disease states noted herein, but in general, this refers to any state so affected by increasing a gut hormone from L cells in a desired manner. The gut hormone system is known in mammals and as such the present invention relates to the treatment of a mammal. In one embodiment, the mammal is a human. Conditions for treatment by increasing a gut hormone from L cells production include, but are not limited to, Type I diabetes, Type II diabetes, obesity, appetite control, metabolic syndrome, and polycystic ovary syndrome.

The gut hormone secretion in the present invention is stimulated in L-cells present in the colon, normally in response to the presence of nutrients in the gut. While such cells are present in other parts of the digestive tract and other parts of the organism, they have the highest concentration in the colon. Stimulation of L-cells in the colon results in the most effective production of gut hormones possible and thus, the most effective treatment. Gut hormones from L-cells of the present invention include, but are not limited to, GLP-1, GP-2, PYY and oxyntomodulin. Incretins such as GLP-1, in particular, are a gut hormone of interest in one embodiment.

The compounds of the invention for stimulating gut hormone release are natural compounds selected from the group comprising butyric acid, a bile acid, a long chain fatty acid, and glutamine. It is understood that this includes combinations of the compounds as well as each compound individually.

As used herein, "a compound" of the present invention includes all compounds described herein.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art, such as x-ray diffraction patterns, solubility, and melting point.

Certain of the compounds described herein, contain one or more chiral centers, or may otherwise be capable of existing as multiple stereoisomers. The scope of the present invention includes mixtures of stereoisomers as well as purified enantiomers or enantiomerically/diastereomerically enriched mixtures. Also, included within the scope of the invention are the individual isomers of the compounds of the present invention, as well as any wholly or partially equilibrated mixtures thereof. The present invention also includes the individual isomers of the compounds represented by the formulas above as mixtures with isomers, thereof, in which one or more chiral centers are inverted.

Typically, but not absolutely, the compounds herein, include the salts of the present compositions and include the pharmaceutically acceptable salts. Salts encompassed within the term "pharmaceutically acceptable salts" refer to non-toxic salts of the compounds of this invention. Salts of the compounds of the present invention may include acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, thethiodide, thmethylammonium, and valerate salts. Other salts, which are not pharmaceutically acceptable, may be useful in the preparation of compounds of this invention, and these should be considered to form a further aspect of the invention.

The "administering" of a composition of the present invention can refer to oral, rectal, IV, IM or the like, and is not dependant on any particular means of administration. As described elsewhere herein, the compounds are so formulated to be taken so as to bypass the upper digestive tract and stomach or rectally to deliver the composition to the colon.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. A therapeutically effective amount will produce a "therapeutic effect".

For use in therapy, therapeutically effective amounts of a compound of the present invention, as well as salts thereof, are presented as a pharmaceutical composition formulated to release in a colon targeted delivery system.

The present invention provides pharmaceutical compositions that include effective amounts of a compound as herein described, or a salt thereof, and one or more pharmaceutically acceptable carriers, diluents, or excipients. The carrier(s), diluent(s) or excipient(s) must be acceptable, in the sense of being compatible with the other ingredients of the formulation and not deleterious to the recipient of the pharmaceutical composition and consistent with the mode of administration, i.e., oral or rectal.

In accordance with another aspect of the invention, there is also provided a process for the preparation of a pharmaceutical formulation, including admixing a compound of the present invention or salts thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the type of colon targeted delivery system are all factors to be considered. The therapeutically effective amount ultimately should be at the discretion of the attendant, physician, or veterinarian. Regardless, an effective amount of a gut hormone compound of the present invention for the treatment of humans suffering from diabetes or an overweight condition and associated conditions, generally, should be in the range of 0.01 to 100 mg/kg body weight of recipient (mammal) per day. More often, the effective amount should be in the range of 0.3 to 30 mg/kg body weight per day. Thus, for a 70 kg adult mammal the actual amount per day would usually be from 21 to 2100 mg. This amount may be given in a single dose per day or in a number (such as two, three, four, five, or more) of sub-doses per day such that the total daily dose is the same. An effective amount of a salt or solvate thereof, may be determined as a proportion of the effective amount of the compound of the present invention per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the present invention, depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

The compounds of the present invention, or a salt thereof, are administered by a targeted drug delivery system. In one embodiment, the delivery systems may be employed for targeting drug delivery to the colon and bypassing the upper digestive system and stomach. Such drug delivery systems include covalent linkage compositions, polymer coated compositions, compositions embedded in matrices, time released compositions, redox-sensitive polymer compositions, bioadhesive compositions, micropartical coating compositions, and osmotic delivery compositions. Suitable compositions include those containing polysaccharides, such as chitosan, pectin, chondroitin sulphate, cyclodexthn, dextrans, guar gum, inulin, amylose and locust bean gum. The compounds may also be coupled with soluble polymers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. Those of particular effectiveness in the present invention include embodiments of multimatrix targeted systems. Of particular effectiveness in the present invention are the targeted matrix in matrix systems comprising a formulation of a hydrophilic first matrix, comprising a lipophilic phase and an amphiphilic phase, wherein the lipophilic phase and the amphiphilic phase are in a second matrix together and the second matrix is dispersed throughout the hydrophilic first matrix and wherein the pharmaceutical composition containing the compound is at least partially incorporated into the amphiphilic phase. Examples of some of the matrix in matrix formulations are disclosed in U.S. Pat. No. 7,431,943 noted above. Those skilled in the art will appreciate the use of such compositions for the purposes of targeting delivery of the compounds of the present invention, or a salt thereof, to the colon of the subject being treated. The methods for the formulation of such compositions for targeted delivery are within the skill in the art, in view of this disclosure.

The compounds of the present invention or a salt thereof may be employed alone or in combination with other therapeutic agents. The compound(s) of the present invention and the other pharmaceutically active agent(s) may be administered together or separately and, when administered separately, administration may occur simultaneously or sequentially, in any order. The amounts of the compound(s) of the present invention and the other pharmaceutically active agent(s) and the relative timings of administration will be selected in order to achieve the desired combined therapeutic effect. The administration in combination of a compound of the present invention or a salt or solvate thereof with other treatment agents may be in combination by administration concomitantly in: (1) a unitary pharmaceutical composition, including both compounds; or (2) separate pharmaceutical compositions, each including one of the compounds. Alternatively, the combination may be administered separately in a sequential manner wherein one treatment agent is administered first and the other second or vice versa. Such sequential administration may be close in time or remote in time.

The compounds may also be formulated in rectal compositions such as suppositories or retention enemas, e.g., containing conventional suppository bases such as cocoa butter or other glycerides. The compositions so formulated will be designed to give an effective dosage to the colon in addition to other areas a rectal administration might affect.

The compounds of the present invention may be used in the treatment of a variety of disorders and conditions. As such, the compounds of the present invention may be used in combination with a variety of other therapeutic agents useful in the treatment of those disorders or conditions. As discussed briefly above, current diabetes therapies include diet, exercise, insulin, insulin secretagogues, glucose-lowering effectors, PPAR-γ agonists, and α-glucosidase inhibitors. The compounds of the present invention may be combined with these or other medical therapies to treat and/or prevent diabetes and associated disorders and conditions, including but not limited to, diabetes Types I and II, obesity, glucose intolerance, insulin resistance, metabolic syndrome, hyperlipidemia, hypercholesterolemia, arteriosclerosis, neurodegenerative diseases, and other indications such as inflammation and stroke. For example, in the treatment of Type II diabetes, a compound of the present invention may be combined with one or more pharmaceutically active agents, including metformin, sulfonylureas such as glyburide and glipizide, repaglinide, nateglinide, thiazolidinediones such as rosiglitazone and pioglitazone, acarbose, miglitol, exanatide, pramlintide, and insulin.

EXAMPLES

Example 1

10 overnight fasted obese diabetic patients with impaired gut hormone effect[3] and/or impaired gut hormone secretion[4,5] are dosed rectally with 1 g of glutamine delivered as an enema. Blood is collected at following time points: −30, −5, 5; 10, 15, 30, and 60 minutes. Blood is analyzed for levels of: glucose, insulin, GLP-1, PYY, and other hormones.

Example 2

10 overnight fasted obese diabetic patients with impaired gut hormone effect[3] and/or impaired gut hormone secretion[4,5] are dosed rectally with suppositories (made as described in[1]) or enema (containing 1 g of glutamine). 30 minutes after drug administration, patients are subjected to Oral Glucose Tolerance Test (OGTT). Blood is collected at following time points: −30, 0, 5, 10, 15, 30, 60, 90, and 120 minutes. Blood is analyzed for levels of: glucose, insulin, GLP-1, PYY, and other hormones. Glucose levels are measured to decrease after treatment regime.

Example 3

10 overnight fasted obese diabetic patients with impaired gut hormone effect[3] and/or impaired gut hormone secretion[4,5] are dosed rectally with suppositories (made as described in[1]) or enema (containing 2 g of butyric acid). 30 minutes after drug administration, patients are subjected to Oral Glucose Tolerance Test (OGTT). Blood is collected at following time points: −30, 0, 5, 10, 15, 30, 60, 90, and 120 minutes. Blood is analyzed for levels of: glucose, insulin, GLP-1, PYY, and other hormones. Glucose levels are measured to decrease after treatment regime.

Example 4

Tables formulated with MMX technology (containing 1 g of glutamine) are made as described in[2]. 10 overnight fasted obese diabetic patients with impaired incretin effect[3] are dosed with one MMX tablet in the morning. 4 hours after drug administration, patients are subjected to Oral Glucose Tolerance Test (OGTT). Blood is collected at following time points: −30, 0, 5, 10, 15, 30, 60, 90, and 120 min. Blood is analyzed for levels of: glucose, insulin, GLP-1, PYY, and other hormones. Glucose levels are measured to decrease after treatment regime.

Example 5

Tables formulated with MMX technology (containing 2 g of butyric acid) are made as described in[2]. 10 overnight fasted obese diabetic patients with impaired incretin effect[3] are dosed with one MMX tablet in the morning. 4 hours after drug administration, patients are subjected to Oral Glucose Tolerance Test (OGTT). Blood is collected at following time points: −30, 0, 5, 10, 15, 30, 60, 90, and 120 min. Blood is analyzed for levels of: glucose, insulin, GLP-1, PYY, and other hormones. Glucose levels are measured to decrease after treatment regime.

Example 6

Tablets formulated with MMX technology (containing 1 g of glutamine) are made as described in[2]. 10 obese diabetic patients with impaired incretin effect[3] are dosed with one MMX tablet in the morning before first meal for six (6) weeks. HbA1c, fasting glucose, and insulin are measured before treatment and at 1, 2, and 6 weeks after initiation of the treatment. Additionally, patients are subjected at these times to Oral Glucose Tolerance Test (OGTT). Blood is collected at following time points: −30, 0, 5, 10, 15, 30, 60, 90, and 120 min. Blood is analyzed for levels of: glucose, insulin, GLP-1, PYY, and other hormones. Glucose levels are measured to decrease after treatment regime.

Example 7

Tables formulated with MMX technology (containing 2 g of butyric acid) are made as described in[2]. 10 obese diabetic patients with impaired incretin effect[3] are dosed with one MMX tablet in the morning before first meal for six (6) weeks. HbA1c, fasting glucose and insulin are measured before the treatment and at 1, 2, and 6 weeks after initiation of the treatment. Additionally, patients are subjected at these times to Oral Glucose Tolerance Test (OGTT). Blood is collected at following time points: −30, 0, 5, 10, 15, 30, 60, 90, and 120 min. Blood is analyzed for levels of: glucose, insulin, GLP-1, PYY, and other hormones. Glucose levels are measured to decrease after treatment regime.

1. Mayo Clin. Proc. 1993, Vol 68, 978 incorporated herein by reference.
2. U.S. Pat. No. 7,431,943 B1 incorporated herein by reference.
3. Diabetes, Obesity and Metabolism, 9 (Suppl. 1), 2007, 23-31 incorporated herein by reference.
4. Toft-Nielsen M B, Damholt M B, Madsbad S et al. Determinants of the impaired secretion of glucagon-like peptide-1 in type 2 diabetic patients. J Clin Endocrinol Metab 2001; 86:3717-3723.
5. Rask E, Olsson T, Soderberg S et al. Impaired incretin response after a mixed meal is associated with insulin resistance in nondiabetic men. Diabetes Care 2001; 24:1640-1645.

What is claimed is:

1. A method of treating type I diabetes, type II diabetes, hypertriglyceridemia, obesity, appetite control, metabolic syndrome, or polycystic ovary syndrome affected by the decrease or lack of release of a gut hormone secreted from L-cells comprising stimulating the production of an L-cell secreted gut hormone in the colon of an individual method comprising the steps of:
    a) selecting a composition causing gut hormone secretion from L-cells from the group comprising butyric acid, and glutamine, the composition formulated to release in a colon targeted delivery system or in a rectal release system; and
    b) administering sufficient stimulating pharmaceutical composition to the individual colon or rectum sufficient to cause a release of gut hormones from the L-cell in the colon of the individual sufficient to achieve the desired result.

2. A method according to claim 1 wherein the composition comprises glutamine.

3. A method according to claim 1 wherein the composition comprises butyric acid.

4. A method according to claim 1 wherein the colon targeted delivery system is a matrix within matrix delivery system.

5. A method according to claim 4 wherein the colon targeted delivery system is a controlled release formulation of a hydrophilic first matrix comprising a lipophilic phase and an amphiphilic phase wherein the lipophilic phase and the amphiphilic phase are in a second matrix together and said second matrix is dispersed throughout the hydrophilic first matrix wherein the agent is at least partially incorporated into the amphiphilic phase.

6. A composition for inducing the release of a gut hormone from L-cells in the colon wherein the composition comprises a composition selected from the group comprising butyric acid, and glutamine formulated such that it does not release in either the stomach or upper gastro intestinal tract.

7. A composition according to claim 6 wherein the composition is formulated in a colon targeted drug delivery system.

8. A composition according to claim 6 wherein the composition is formulated for rectal administration.

9. A composition according to claim 6 wherein the composition comprises glutamine.

10. A composition according to claim 6 wherein the composition comprises butyric acid.

11. A composition according to claim 7 wherein the colon targeted delivery system is a matrix within matrix system.

12. A composition according to claim 11 wherein the colon targeted delivery system is a controlled-release formulation of a hydrophilic first matrix comprising a lipophilic phase and an amphiphilic phase wherein the lipophilic phase and the amphiphilic phase are in a second matrix together and said second matrix is dispersed throughout the hydrophilic first matrix wherein the composition is at least partially incorporated into the amphiphilic phase.

* * * * *